Figure 1:
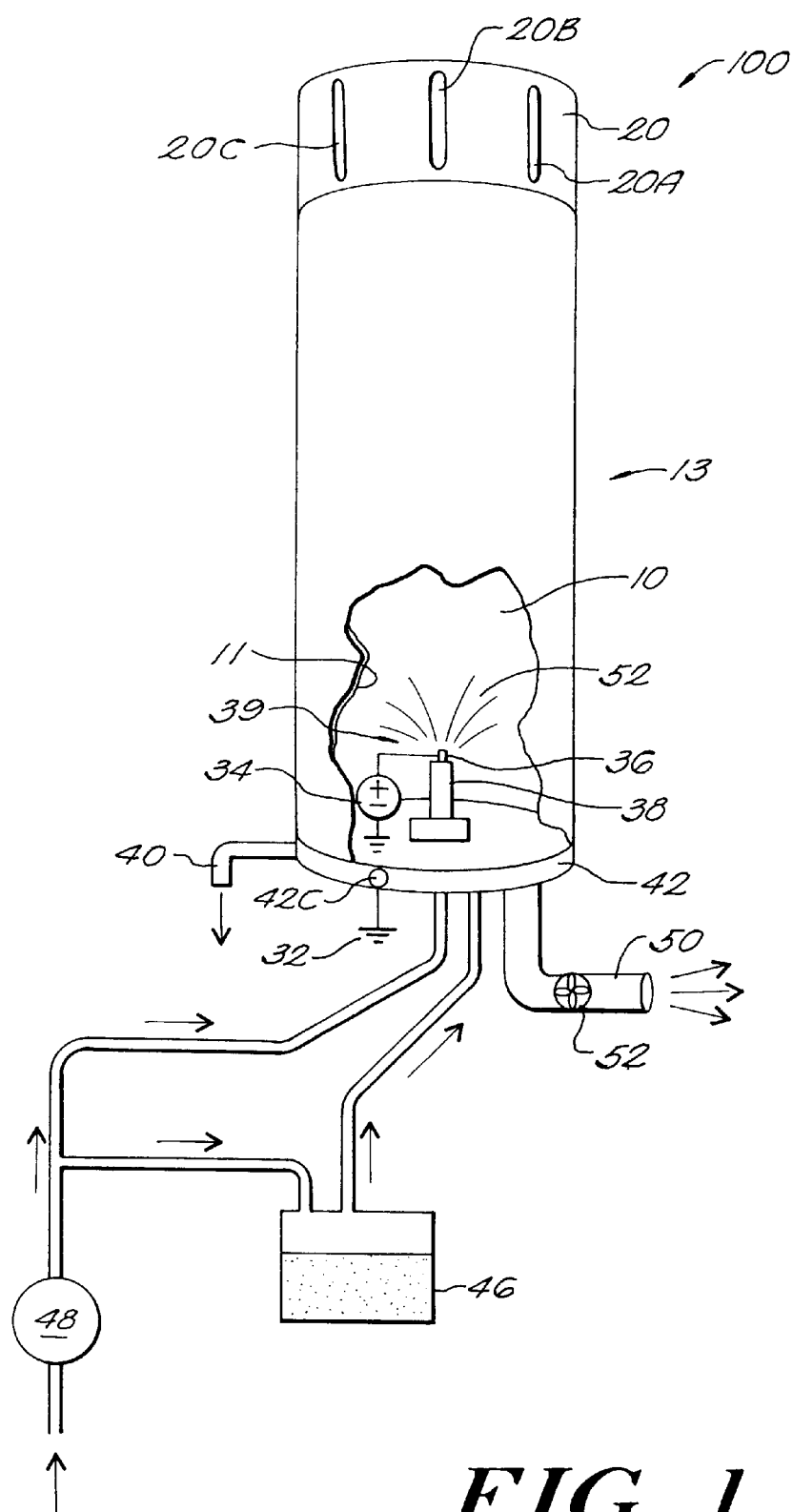

United States Patent

Imbaro et al.

[11] Patent Number: 5,914,454
[45] Date of Patent: Jun. 22, 1999

[54] APPARATUS AND METHOD FOR CONCENTRATING CONSTITUENTS FROM A GAS STREAM

[75] Inventors: Robert L. Imbaro, Dedham; Erich A. Dieffenbach, Hudson, both of Mass.

[73] Assignee: Team Technologies, LLC, Newton, Mass.

[21] Appl. No.: 08/928,382

[22] Filed: Sep. 12, 1997

[51] Int. Cl.⁶ .................................................. B03C 3/014
[52] U.S. Cl. .................... 95/64; 95/71; 95/78; 96/27; 96/53; 96/61; 261/79.2
[58] Field of Search .................... 95/64, 65, 71, 95/78; 96/27, 52, 53, 61, 64, 74; 261/79.2

[56] References Cited

U.S. PATENT DOCUMENTS

| Re. 30,479 | 1/1981 | Cohen et al. | 95/71 |
|---|---|---|---|
| 3,855,367 | 12/1974 | Webb | 261/79.2 X |
| 3,988,128 | 10/1976 | Hogg | 96/27 X |
| 4,398,928 | 8/1983 | Kunsagi | 96/27 |
| 5,213,595 | 5/1993 | Kim | 96/53 X |
| 5,466,270 | 11/1995 | Abdelmalek | 261/79.2 X |
| 5,565,180 | 10/1996 | Spink | 423/220 |
| 5,639,025 | 6/1997 | Bush | 239/333 |
| 5,639,026 | 6/1997 | Woods | 239/394 |

FOREIGN PATENT DOCUMENTS 52-74961  6/1977  Japan .......................................... 96/27

*Primary Examiner*—Richard L. Chiesa
*Attorney, Agent, or Firm*—Lahive & Cockfield, LLP

[57] ABSTRACT

An apparatus for sampling a gas stream and concentrating selected constituents found therein. The apparatus includes a collection chamber into which a gas stream is drawn and a nozzle which sprays charged droplets of a collection fluid countercurrent to the gas stream. The charged droplets, now containing the selected constituents, are propelled to the wall under the influence of an electrostatic force and collected in a collection well at the bottom of the collection chamber. The apparatus can include a cyclonic flow inducer which imparts a circumferential component to the gas stream velocity, thereby enhancing collection efficiency by increasing the residency time of the gas stream within the collection chamber.

30 Claims, 3 Drawing Sheets

APPARATUS AND METHOD FOR CONCENTRATING CONSTITUENTS FROM A GAS STREAM

This invention relates generally to the field of gas sampling devices, and in particular to devices and methods for concentrating constituents such as particles or trace elements from a gas.

BACKGROUND

The ability to detect constituents such as particles or trace chemicals in a gas offer numerous applications. For example, it is known that a hidden cache of explosive material sheds trace amounts of materials into the air. Similarly, the presence at the site of a recent fire of certain organic compounds in the air is evidence of an arsonist's use of an accelerant. Detection of airborne bacteria, viruses, molds and other living matter can assist epidemiologists in monitoring and controlling the spread of disease.

The detection of airborne constituents by known techniques generally involves two steps. First, the constituents are collected, and second, they are analyzed. Analysis can be performed, for example, by passing the sample through a mass spectrometer, by gas chromatography, or even visually. The collection step generally requires that the constituents be made available in sufficient concentration for the analysis step to be performed. The sufficiency of concentration depends on the sensitivity of the analyzer and on the nature of the constituent to be detected.

Where the concentration of the selected constituent in ambient air is insufficient to permit the analyzer to function, the selected constituent must first be concentrated before they can be analyzed. Conventional methods of concentrating selected constituents include passing air through a filter and, after sufficient time has elapsed to build up the required concentration of constituents on the filter, collecting the residue from the filter for analysis.

Because in practice the concentration of particles in air is extremely low, it becomes necessary to pass large volumes of air through the filter in order to collect sufficient residue on a filter for analysis. The time required to pass large volumes of air through the filter and the additional time required to remove the residue from the filter and to prepare it for analysis make this method impractical where rapid response is necessary.

The air sampling process can be accelerated to some extent by increasing the volume rate of flow through the filter. However, the mechanical resistance of a filter to fluid flow increases as the fluid velocity increases. As a result, the energy required to force the fluid through the filter increases. Moreover, if the fluid velocity is too high, the fluid force on the filter may cause the filter to rupture.

This conventional method of concentration is unable to concentrate trace gases from ambient air because such gases can generally pass through the filter. Moreover, where the particles are microorganisms, the large volume of air can desiccate any microorganisms already trapped by the filter, thereby destroying the viability of the sample.

Consequently, there is a need in the art for a device which can rapidly and efficiently collect and concentrate airborne constituents of a gas stream for subsequent analysis.

SUMMARY

An apparatus according to the invention concentrates selected constituents from a gas stream by introducing the gas stream into a collection chamber having grounded walls and spraying electrically charged droplets of a selected conductive collection fluid countercurrent to the gas stream.

The apparatus includes a collection chamber into which a gas stream containing particles or other constituents to be concentrated is drawn. A nozzle or similar device sprays droplets of collection fluid into the chamber in a direction counter to that in which the gas stream travels. The nozzle and the wall of the collection chamber are connected across a high voltage source, thereby creating an electrostatic force that propels the droplets to the wall. The droplets on the wall, now carrying particles or other constituents from the gas stream, flow to a collection well at the bottom of the collection chamber from which they are collected and made available for analysis.

To enhance collection efficiency, an apparatus according to the invention can further include a component for increasing the residency time of the gas stream in the collection chamber. In the preferred embodiment, this component is a cyclonic flow inducer which imparts a circumferential component of velocity to the gas stream, thereby increasing the path length followed by the gas stream within the collection chamber.

These and other features, aspects, and advantages of the invention will be better understood with reference to the following description and the accompanying drawings in which:

BRIEF DESCRIPTION OF THE DRAWINGS

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions.

FIG. 1 is a cutaway view of an air sampler according to the invention;

FIG. 2A is an elevation view of the cyclonic inducer shown in FIG. 1;

FIG. 2B is a cross-sectional view of the cyclonic inducer shown in FIG. 2A;

FIG. 2C is a cross-sectional view of the cyclonic inducer shown in FIG. 2A in which the fluid passageway is tangent to the circle formed by the inner wall of the cyclone inducer;

FIG. 3 is a cross-sectional view of the nozzle depicted in FIG. 1 showing a cut-away view of the collection fluid chamber; and FIG. 4 is a cross-sectional view through the base of the air sampler of FIG. 1.

DETAILED DESCRIPTION OF THE PREFERRED EMBODIMENT

The illustrated embodiment is an air sampler 100 for collecting selected constituents from a gas stream and concentrating them in a conductive collection fluid, typically a mixture of distilled water, a wetting agent, and a conductive salt, which can later be removed for analysis. The composition of the collection fluid can be tailored to whatever is to be collected from the gas stream. For example, to collect a basic compound such as ammonia, the collection fluid can be made acidic. Conversely, collection of an acidic compound may require a basic collection fluid. Collection of microorganism is most effective with a saline solution.

The illustrated air sampler includes a base 42 supporting a housing 13 having a chamber wall 11 which forms a collection chamber 10 into which a gas stream is drawn by a blower 52 through slots 20A, 20B, 20C of a cyclonic inducer 20 and expelled through an exhaust pipe 50. A nozzle assembly 39 mounted on the base 42 injects an atomized spray of collection fluid 52 into the collection chamber 10. As a result of having been charged by a high voltage source 34, the droplets forming the atomized spray 52 are electrically charged.

The collection chamber 10 is a cylindrical space enclosed by the chamber wall 11 and having a circular cross section. In the preferred embodiment, the chamber wall 11 is an inert and transparent material such as glass or plastic to permit visual inspection during operation and to prevent contamination of the sample. Those of ordinary skill will readily recognize that the chamber wall 11 of the air sampler, and thus the collection chamber 10, can have any geometric shape. Additionally, the chamber wall 11 and other components can be made of any other material suitable for use with the operating environment of the sampler.

Figure 4:
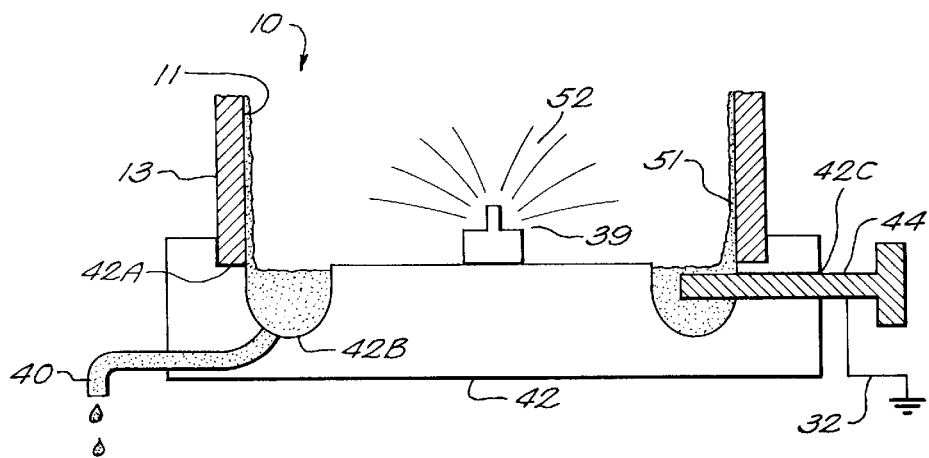

As best seen in FIG. 4, the housing 13 rests on a lip 42A adjacent to a collection well 42B formed by cutting a circular groove in the base 42. A sample output 40 drains from the collection well. A conducting bolt 44 connected to a grounding wire 32 passes through a hole 42C in the base 42 and into the collection well 42B. The collection well 42B and the sample output 40 are preferably made of an inert material such as polytetrafluoroethylene (TEFLON) to prevent contamination of the sample.

Figure 2A:
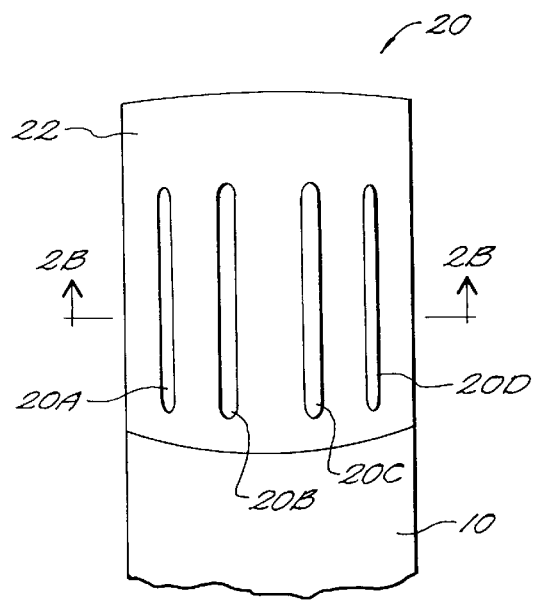
Figure 2B:
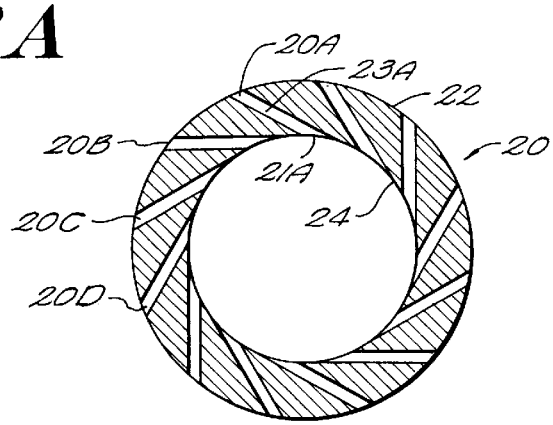
Figure 2C:
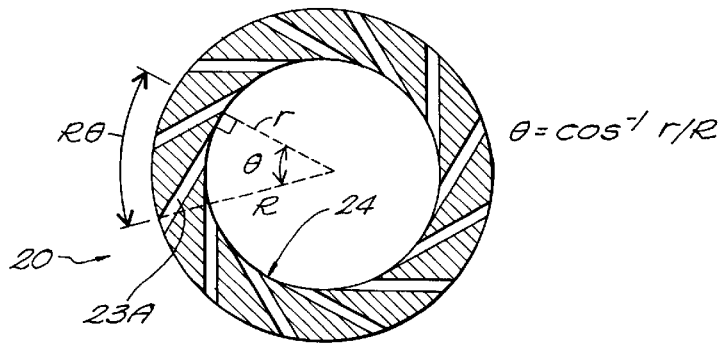

The cyclonic inducer 20, depicted in FIG. 2A and FIG. 2B, is a cylindrical structure mounted to or seated on the housing 13 and having a circular outer wall 22 and a circular inner wall 24 concentric with the outer wall 22. A plurality of fluid openings 20A, 20B, 20C, 20D perforate the outer wall 22. Each such opening in the outer wall 22, of which 20A is representative, is connected by a passageway 23A to a corresponding opening 21A in the inner wall. According to a preferred practice, each opening in the outer wall is circumferentially offset from its corresponding opening in the inner wall in such a way as to prevent gas from flowing along the radius of the circle formed by the inner wall of the cyclonic inducer. A line connecting the opening in the inner wall and the opening in the outer wall is thus collinear with a chord of a circle defined by the outer wall. In a preferred embodiment, the inner and outer openings are circumferentially offset such that one wall of the passageway 23A is tangent to the circle formed by the inner wall 24 of the cyclonic inducer 20 as shown in FIG. 2C.

The geometry of the cyclonic inducer described above ensures that gas drawn into the openings 20A, 20B, 20C of the cyclonic inducer 20 enters the collection chamber 10 having a component of velocity tangent to the inner wall 24 of the cyclonic inducer 20. When combined with the component of velocity parallel to the chamber wall 11, the streamlines followed by the gas stream in the collection chamber 10 are spiral. This enhances collection efficiency by increasing the path length traversed by the gas stream in the collection chamber and hence the residence time of the gas within the collection chamber.

Figure 3:
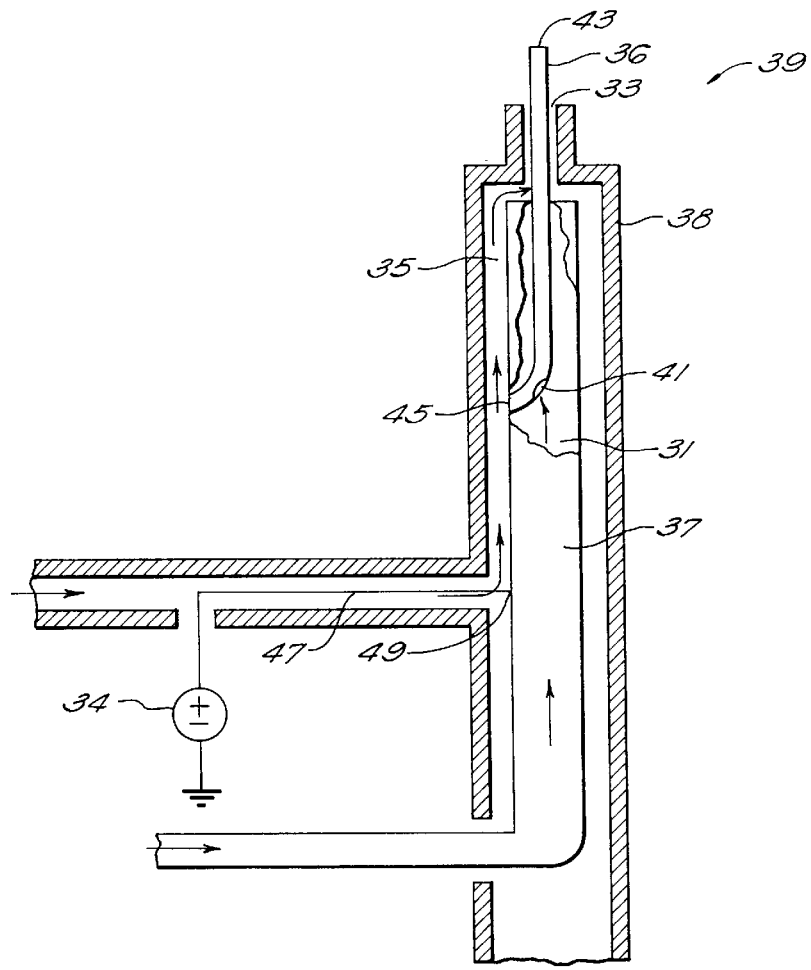

With reference to FIGS. 1 and 3, the nozzle assembly 39 includes an outer tube 38 and an electrically conductive inner wall 37 concentric with the outer tube 38. Together, the outer tube 38 and the inner wall 37 form an annular lumen 35 connected to a compressed air source 48 which opens into the collection chamber 10 at an annular compressed air orifice 33. The inner wall 37 forms a collection fluid chamber 31 connected to a collection fluid reservoir 46.

In the illustrated embodiment, the inner wall 37 and the outer tube 38 are circular in cross section. Those of ordinary skill will readily recognize that the inner wall 37 and the outer tube 38, and thus the annular lumen 35 and the collection fluid chamber 31, can have any geometric shape.

An electrically conductive hollow needle 36 extends into the collection chamber 10 at its proximal end and into the collection fluid chamber 31 at its distal end. A collection fluid orifice 43 at the distal end of the hollow needle 36 and a fluid entrance 41 at the proximal end of the hollow needle permit fluid communication between the collection fluid chamber 31 and the collection chamber 10. As depicted in FIG. 3, the collection fluid orifice 43 is axially spaced from and distal to the compressed air orifice 33, and oriented to spray collection fluid in a direction counter current (i.e., from bottom to top) to the flow of the gas stream (i.e., flowing top to bottom) from the cyclonic inducer 20 to the exhaust pipe 50.

In the illustrated embodiment, the hollow needle 36 and the collection fluid orifice 43 are circular in cross section and the fluid entrance 41 is circular. Those of ordinary skill will readily recognize that the hollow needle 36, the collection fluid orifice 43, and the fluid entrance 41 can have any geometric shape.

Compressed air flowing through the annular compressed air orifice 33 upstream from the collection fluid orifice 43 creates a low-pressure zone surrounding the collection fluid orifice 43. This low pressure zone draws the collection fluid downstream and into the collection chamber and atomizes it into small droplets. By introducing compressed air upstream from the collection fluid, the nozzle can atomize the collection fluid even at collection fluid flow rates as low as 1 mL/minute. The nozzle 39 can achieve atomization at low flow rates without degradation in the quality of atomization and without triggering the onset of self-excited pulsation.

At its proximal end, the needle 36 makes electrical contact 45 with the conductive inner wall 37 which in turn makes electrical contact 49 with a wire 47 connected to a high voltage source 34. The high-voltage source 34 should be operated at a voltage sufficient to drive the charged droplets to the chamber wall 11 before they can reach the top of the collection chamber 10 but not high enough to cause arcing between the charged droplets and the chamber wall 11. In the illustrated embodiment, the high-voltage source 34 is typically operated at 25,000 volts. However, the optimal voltage setting can depend on the size and shape of the collection chamber 10, the conductivity of the collection fluid, and the breakdown voltage of the gas stream.

Because of the electrical contact 45 between the hollow needle 36 and the inner wall 37, an electric field exists in the space within the hollow needle 36. Collection fluid entering the hollow needle 36 through the entrance 41 is exposed to this electric field and acquires a charge as a result.

In steady-state operation, the blower 52 shown in FIG. 1 creates a partial vacuum in the collection chamber 10 thereby drawing ambient air through the openings 20A–20C in the outer wall 22 of the cyclonic inducer 20 and forming a gas stream. This gas stream is directed by the fluid passageways, for example, fluid passageway 23A, to the corresponding openings 21A in the inner wall of the cyclonic inducer 20. As a result of having entered the interior of the cyclonic inducer along a chord rather than along a radius of the circle formed by the inner wall 24 of the cyclonic inducer 20, the gas stream now has a tangential component of velocity. This tangential component combines with the downward component of velocity supplied by the blower 52 to create a downwardly spiraling flow field in the collection chamber 10.

Meanwhile, pressurized air from the compressed air source 48 enters the annular lumen 35 of the nozzle 39 and exits into the collection chamber 10 through the compressed air orifice 33. The pressurized air also drives collection fluid from the collection fluid reservoir 46 into the fluid chamber 31 of the nozzle 39, through the fluid entrance 41 of the hollow needle 36, and into the collection chamber 10 through the collection fluid orifice 43. Because the collection fluid orifice 43 is located downstream from (i.e., is axially spaced from) the compressed air orifice 33, air moving at high velocity surrounds the collection fluid orifice 43, thereby forming a low pressure zone which draws the collection fluid upward, forming a conical spray 52 of small droplets in the process. In the preferred embodiment, these droplets are on the order of 10 microns or less in diameter.

The rate at which collection fluid flows out of the collection fluid orifice 43 can be varied from 1 cc/minute to 5 cc/minute but is preferably maintained below 2 cc/minute to prevent wetting of the nozzle and potential arcing.

As the collection fluid passes through the hollow needle 36 on its way to the collection fluid orifice 43, it is exposed to an electric field created by the connection 49 between the conductive inner wall 37 and the high voltage source 34. This electric field induces a charge on the collection fluid. The spray 52 of atomized collection fluid at the nozzle 39 therefore consists of charged droplets susceptible to motion under the influence of an electrostatic force.

In an initial, start-up phase of operation, a portion of the droplets forming the conical spray 52 strikes the wall 11 of the collection chamber 10. Gravity draws these droplets down the wall of the collection chamber to the collection well 42B formed in the base 42. After a brief period of operation, the level of collection fluid in the well rises to the point at which the conducting bolt 44 is immersed in the collection fluid. Since the conducting bolt 44 is connected to a grounding wire 32, the collection fluid in the well 42B discharges.

After continued operation, the illustrated air concentrator enters a steady-state phase in which the collection fluid coats the chamber wall 11 and thereby forms an electrically continuous path 51, best seen in FIG. 4, between the collection fluid in contact with the conductive bolt 44 and the collection fluid coating the wall 11. Once this occurs, an electric field exists between the charged droplets of collection fluid in the spray 52 and the collection fluid coating the wall 11.

The electrostatic force on the charged droplets that results from this electric field propels the charged droplets to the chamber wall 11. Between the time the droplets first enter the chamber 10 and the time they strike the chamber wall 11 in response to this electrostatic force, they can collide with one or more selected constituents carried by the gas stream. If after having collided with a selected constituent the droplets strike the chamber wall 11, the droplets carry the selected constituent to the wall. The droplets then flow down the wall 11 of the collection chamber in response to gravity, carrying with them the constituent to be collected.

The droplets accumulate in the collection well 42B cut into the base 42. These accumulated droplets can then be drained from the collection well 42B through the sample output 40 for analysis of the selected constituents concentrated therein. In the illustrated embodiment, the time between the capture of a selected constituent and the availability of a sample containing that selected constituent at the sample output 40, referred to as the "dwell time," is approximately thirty seconds.

The concentration of selected constituents in each droplet depends on the concentration of selected constituents in the gas stream and on the efficiency with which the selected constituents are adsorbed by the charged droplets. It can be seen therefore that on the average, the concentration of selected constituents captured by one charged droplet is the same as the concentration of selected constituents captured by any other droplet. Consequently, an air sampler according to the invention can produce a sample for analysis without the need to wait for the concentration of selected constituents to build up over time as is the case in conventional air samplers employing filters.

Moreover, it can be seen that the concentration of selected constituents in each droplet is likely to be greater than the concentration of selected constituents in the gas because each droplet can capture, in its limited volume, airborne constituents from a volume as large as the path length of the droplet times the effective cross section of the droplet integrated over the path length. Additionally, any selected constituent that eludes capture by a charged droplet in this manner is available for capture by another droplet for as long as the selected constituent is within the collection chamber. As a result, an air sampler according to the invention can concentrate selected constituents from a gas stream within the collection chamber.

A significant advantage of the present invention is the ability of the air sampler to concentrate selected constituents contained in large volumes of air into small quantities of collection fluid. Up to $10^6$ parts of air can be highly and efficiently concentrated into one part of collection fluid at collection efficiencies ranging between about 65% to about 100% depending on the contaminant involved. This results in samples having analytic sensitivities in the range of approximately one part per trillion to one part per quadrillion. This offers orders of magnitude greater sensitivity than conventional systems having sensitivities ranging from parts per million to parts per billion.

It is further apparent that the air sampler 100 of the invention can, with a suitable choice of collection fluid, collect and concentrate gaseous constituents of a gas mixture by adsorption of the desired gaseous constituent on the charged droplets. The apparatus of the invention can also collect and concentrate airborne microorganisms in a biologically hospitable collection fluid such as saline. In each case, the operation of the apparatus is as set forth above.

The collection efficiency of the air sampler 100 can be improved by increasing the length of time, referred to as the "residency time," that the airborne constituents are bombarded by charged droplets. Increasing the residency time greatly increases the likelihood of a collision between an airborne selected constituent and a charged droplet. This increase in residency time can be accomplished by increasing the path length traversed by the gas stream in the collection chamber 10. In the preferred embodiment, this increased path length results from the use of the cyclonic inducer 20 to add a tangential component to the otherwise axial velocity of the gas stream and thereby create a downward spiral flow in the gas stream. In the preferred embodiment, the use of the cyclonic inducer having passageways tangent to the circle formed by the inner wall as set forth above results in residence times of about 0.2 seconds during which each selected constituent can be bombarded by as many as $10^6$ charged droplets.

To further increase collection efficiency, the air sampler 100 of the present invention maximizes the likelihood that a collision between a selected constituent and a droplet results in agglomeration of the selected constituent by the droplet by increasing the relative velocity between the charged droplets and the gas stream. It does so by introducing the charged droplets in a direction countercurrent to the direction of the fluid stream.

The collection efficiency of the air sampler of the invention varies depending on the contaminant to be sampled. However, the following table summarizes typical values:

| Challenge | Capture Efficiency, % |
|---|---|
| 1.305μ poly. sty. selected constituents | 74%–79% |
| 0.78μ poly. sty. selected constituents | 84%–90% |
| 0.56μ poly. sty. selected constituents | 73%–96% |
| 0.36μ poly. sty. selected constituents | 75% |
| NOx gases | 80% |
| SOx gases | 75%–100% |
| Acetone | 95% |
| Acetonitrile Acetic Acid Vapor | 93% |
| Ammonia | 98% |
| Benzene | 98% |
| Butyl Acetate | 98% |
| Carbon Disulfide | 87% |
| Chlorobenzene | 93% |
| Chloroform | 89% |
| o-Dichlorobenzene | 97% |
| Diethylbenzene | 90% |
| p-Dioxane | 96% |
| Ethyl Acetate | 98% |
| Formaldehyde | 95% |
| Freon | 64% |
| Heptane | 97% |
| Hexanes | 95% |
| Methanol | 94% |
| Toluene | 86% |
| Xylene | 93% |

It will thus be seen that the invention efficiently attains the objects set forth above. Since certain changes may be made in the above constructions without departing from the scope of the invention, it is intended that all matter contained in the above description or shown in the accompanying drawings be interpreted as illustrative and not in a limiting sense.

It is also to be understood that the following claims are intended to cover all generic and specific features of the invention described herein, and all statements of the scope of the invention which as a matter of language might be said to fall there between.

Having described the invention, what is claimed as new and secured by Letters Patent is:

1. A gas sampling apparatus for concentrating a constituent from an input fluid stream having an input fluid flow, said apparatus comprising a housing forming a collection chamber defined by a chamber wall, a cyclonic inducer element forming a cap portion that mounts to a top portion of said housing for transforming said input fluid flow into a cyclonic fluid flow through said collection chamber, said cyclonic inducer element including an inner wall and an outer wall extending along a longitudinal axis, and means forming fluid passages between said inner and outer walls, at least one of said fluid passages opening onto said inner wall at a first circumferential location and opening onto said outer wall at a second circumferential location different from said first circumferential location, spray means for introducing an atomized spray of a collection fluid into said collection chamber, said collection fluid being adapted to remove at least a portion of said constituent from said input fluid through collision, said spray means including a nozzle in fluid communication with said collection chamber, said nozzle including means forming a first fluid conduit for introducing a selected fluid into said collection chamber, and means forming a second fluid conduit for introducing a collection fluid into said chamber, wherein said first fluid conduit is configured to introduce the selected fluid into said collection chamber at a location upstream from a location where said second fluid conduit introduces the collection fluid into said collection chamber, and electric potential means for creating an electrostatic potential between said chamber wall and said collection fluid, thereby creating an electrostatic force between said chamber wall and said spray to collect said constituent component on said chamber wall.

2. The apparatus of claim 1, wherein at least one of said fluid passages is arranged to form a chord of a circle defined by said outer wall of said cyclonic inducer element.

3. The electrostatic precipitator of claim 1, wherein said cyclonic inducer element is adapted to increase the residence time of said constituent component cyclonic fluid flow in said collection chamber, thereby increasing the amount of constituent component collected from said fluid flow.

4. The apparatus of claim 1, wherein said spray means comprises a nozzle coupled to said housing, said spray means having means forming a first fluid conduit for introducing a selected fluid into said collection chamber and a second fluid conduit for introducing a collection fluid into said collection chamber.

5. The apparatus of claim 4, wherein said first fluid conduit introduces the selected fluid into said collection chamber at a location upstream from a location at which said second fluid conduit introduces the collection fluid into said chamber.

6. The apparatus of claim 4, wherein said nozzle has a tip portion, and said second fluid conduit terminates at an outermost end of said tip portion, and wherein said first fluid conduit terminates at a location axially spaced from said outermost end at said tip portion.

7. The apparatus of claim 4, further including means for energizing said second fluid conduit to impart a potential to the collection fluid passing therethrough.

8. The apparatus of claim 7, wherein said means for energizing comprises an electrode in contact with a wall of said second fluid conduit.

9. A method for concentrating a constituent from an input fluid stream, said method comprising the steps of providing a housing forming a collection chamber defined by a chamber wall, mounting a cyclonic inducer element to a top portion of said housing for transforming said input fluid flow into a cyclonic fluid flow through said collection chamber, said cyclonic inducer element including an inner wall and an outer wall, both extending along a longitudinal axis, providing a plurality of fluid passages between said inner and outer walls such that at least one of said fluid passages opens onto said inner wall at a first circumferential location and opens onto said outer wall at a second circumferential location different from said first circumferential location, introducing an atomized spray of a collection fluid into said collection chamber by providing a nozzle coupled to said housing, said nozzle having a first fluid conduit for introducing a selected fluid into said chamber and a second fluid conduit for introducing a collection fluid into said chamber, said first conduit configured to introduce the selected fluid into said chamber at a location upstream from a location where said second fluid conduit introduces the collection fluid into said chamber, said collection fluid being adapted to remove at least a portion of said constituent component from said input fluid through collision, and creating an electrostatic potential between said wall and said collection fluid, thereby creating an electrostatic force between said chamber wall and said spray to collect said constituent component on said chamber wall.

10. The method of claim 9, further comprising the step of transferring said cyclonic fluid flow to said collection chamber.

11. The method of claim 9, further comprising the step of arranging at least one of said fluid passages to form a chord of a circle defined by said outer wall of said cyclonic inducer element.

12. The method of claim 9, further comprising the step of increasing the residence time of fluid within said collection chamber by forming a cyclonic fluid flow with said cyclonic inducer element.

13. The method of claim 9, further comprising the step of increasing the amount of the constituent component collected from said fluid flow by forming a cyclonic fluid flow with said cyclonic inducer element.

14. The method of claim 9, further including the step of energizing the second fluid conduit to impart an electrical potential to the collection fluid when passing therethrough.

15. The method of claim 9, wherein said nozzle has a tip portion, said method further comprising the steps of terminating said second fluid conduit at an outermost end of said tip portion and terminating said first fluid conduit at a location axially spaced from said outermost end at said tip portion.

16. A gas sampling apparatus for concentrating a constituent from an input fluid stream having an input fluid flow, said apparatus comprising a housing forming a collection chamber defined by a chamber wall, a cyclonic inducer element forming a cap portion that mounts to a top portion of said housing for transforming said input fluid flow into a cyclonic fluid flow through said collection chamber, said cyclonic inducer element including an inner wall and an outer wall extending along a longitudinal axis, and means forming fluid passages between said inner and outer walls, at least one of said fluid passages forming a tangent to a circle defined by said inner wall of said cyclonic inducer element, spray means for introducing an atomized spray of a collection fluid into said collection chamber, said collection fluid being adapted to remove at least a portion of said constituent from said input fluid through collision, said spray means including a nozzle in fluid communication with said collection chamber, said nozzle including means forming a first fluid conduit for introducing a selected fluid into said collection chamber, and means forming a second fluid conduit for introducing a collection fluid into said chamber, wherein said first fluid conduit is configured to introduce the selected fluid into said collection chamber at a location upstream from a location where said second fluid conduit introduces the collection fluid into said collection chamber, and electric potential means for creating an electrostatic potential between said chamber wall and said collection fluid, thereby creating an electrostatic force between said chamber wall and said spray to collect said constituent component on said chamber wall.

17. The apparatus of claim 16, wherein at least one of said fluid passages is arranged to form a chord of a circle defined by said outer wall of said cyclonic inducer element.

18. The electrostatic precipitator of claim 16, wherein said cyclonic inducer element is adapted to increase the residence time of said constituent component cyclonic fluid flow in said collection chamber, thereby increasing the amount of constituent component collected from said fluid flow.

19. The apparatus of claim 16, wherein said spray means comprises a nozzle coupled to said housing, said spray means having means forming a first fluid conduit for introducing a selected fluid into said collection chamber and a second fluid conduit for introducing a collection fluid into said collection chamber.

20. The apparatus of claim 19, wherein said first fluid conduit introduces the selected fluid into said collection chamber at a location upstream from a location at which said second fluid conduit introduces the collection fluid into said chamber.

21. The apparatus of claim 19, further including means for energizing said second fluid conduit to impart a potential to the collection fluid passing therethrough.

22. The apparatus of claim 21, wherein said means for energizing comprises an electrode in contact with a wall of said second fluid conduit.

23. The apparatus of claim 19, wherein said nozzle has a tip portion, and said second fluid conduit terminates at an outermost end of said tip portion, and wherein said first fluid conduit terminates at a location axially spaced from said outermost end at said tip portion.

24. A method for concentrating a constituent from an input fluid stream, said method comprising the steps of providing a housing forming a collection chamber defined by a chamber wall, mounting a cyclonic inducer element to a top portion of said housing for transforming said input fluid flow into a cyclonic fluid flow through said collection chamber, said cyclonic inducer element including an inner wall and an outer wall, both extending along a longitudinal axis, providing a plurality of fluid passages between said inner and outer walls, at least one of said fluid passages forming a tangent to a circle defined by said inner wall of said cyclonic inducer element, introducing an atomized spray of a collection fluid into said collection chamber by providing a nozzle coupled to said housing, said nozzle having a first fluid conduit for introducing a selected fluid into said chamber and a second fluid conduit for introducing a collection fluid into said chamber, said first conduit configured to introduce the selected fluid into said chamber at a location upstream from a location where said second fluid conduit introduces the collection fluid into said chamber, said collection fluid being adapted to remove at least a portion of said constituent component from said input fluid through collision, and creating an electrostatic potential between said wall and said collection fluid, thereby creating an electrostatic force between said chamber wall and said spray to collect said constituent component on said chamber wall.

25. The method of claim 24, further comprising the step of transferring said cyclonic fluid flow to said collection chamber.

26. The method of claim 24, further comprising the step of arranging at least one of said fluid passages to form a chord of a circle defined by said outer wall of said cyclonic inducer element.

27. The method of claim 24, further comprising the step of increasing the residence time of fluid within said collection chamber by forming a cyclonic fluid flow with said cyclonic inducer element.

28. The method of claim 24, further comprising the step of increasing the amount of the constituent component collected from said fluid flow by forming a cyclonic fluid flow with said cyclonic inducer element.

29. The method of claim 24, further including the step of energizing the second fluid conduit to impart an electrical potential to the collection fluid when passing therethrough.

30. The method of claim 24, wherein said nozzle has a tip portion, said method further comprising the steps of terminating said second fluid conduit at an outermost end of said tip portion and terminating said first fluid conduit at a location axially spaced from said outermost end at said tip portion.

\* \* \* \* \*